United States Patent
Song et al.

(10) Patent No.: US 10,188,579 B2
(45) Date of Patent: Jan. 29, 2019

(54) METHOD FOR CONTROLLING A WALKING ASSISTANT APPARATUS

(71) Applicant: NATIONAL CHIAO TUNG UNIVERSITY, Hsinchu (TW)

(72) Inventors: Kai-Tai Song, New Taipei (TW); Shang-Yang Wu, Taoyuan (TW); Sin-Yi Jiang, New Taipei (TW)

(73) Assignee: National Chiao Tung University, Hsinchu (TW)

( * ) Notice: Subject to any disclaimer, the term of this patent is extended or adjusted under 35 U.S.C. 154(b) by 0 days.

(21) Appl. No.: 15/368,316

(22) Filed: Dec. 2, 2016

(65) Prior Publication Data
US 2017/0189259 A1 Jul. 6, 2017

(30) Foreign Application Priority Data
Jan. 6, 2016 (TW) .............................. 105100238 A

(51) Int. Cl.
*A61H 3/04* (2006.01)
*A61B 5/11* (2006.01)
(Continued)

(52) U.S. Cl.
CPC .................. *A61H 3/04* (2013.01); *A61B 5/11* (2013.01); *A61B 5/112* (2013.01); *A61B 5/6887* (2013.01);
(Continued)

(58) Field of Classification Search
CPC ................ A61H 3/04; A61H 2003/043; A61H 2201/0173; A61H 2011/1207;
(Continued)

(56) References Cited

U.S. PATENT DOCUMENTS 6,371,890 B1 *  4/2002  Schell .................. B60W 10/06
                                                         477/209
6,645,126 B1 * 11/2003  Martin ............... A63B 69/0059
                                                            482/3
(Continued)

FOREIGN PATENT DOCUMENTS

CN      202015325 U    10/2011
CN      202397747 U     8/2012
(Continued)

OTHER PUBLICATIONS

Liao, et al., "Vision based Gait Analysis on Robotic Walking Stabilization System for Patients with Parkinson's Disease," in Proc. of 2014 IEEE International Conference on Automation Science and Engineering (CASE), Taipei, Taiwan, Aug. 18-22, 2014, pp. 818-823.
(Continued)

*Primary Examiner* — Calvin Cheung
(74) *Attorney, Agent, or Firm* — Lewis Roca Rothgerber Christie LLP

(57) ABSTRACT

A method for controlling a walking assistant apparatus includes: scanning a user so as to generate information associated with gait of the user; detecting a torque applied to a torque sensor; estimating a speed of the user based on the information; calculating a compliant motion speed, and a compliant rotational speed; and controlling the motion unit to move at the compliant motion speed and to turn at the compliant rotational speed. This disclosure provides an autonomous obstacle avoidance mechanism; by combining the obstacle avoidance mechanism and the compliance controls, the walking-assistance apparatus is able to help user prevent from collisions with obstacles when walking in an environment with obstacles.

10 Claims, 15 Drawing Sheets

(51) Int. Cl.
*A61B 5/00* (2006.01)
*A61F 4/00* (2006.01)

(52) U.S. Cl.
CPC ............... *A61F 4/00* (2013.01); *A61B 5/1126* (2013.01); *A61H 2003/043* (2013.01); *A61H 2201/0173* (2013.01); *A61H 2201/1207* (2013.01); *A61H 2201/1635* (2013.01); *A61H 2201/5007* (2013.01); *A61H 2201/5043* (2013.01); *A61H 2201/5058* (2013.01); *A61H 2201/5064* (2013.01); *A61H 2201/5069* (2013.01); *A61H 2201/5079* (2013.01)

(58) Field of Classification Search
CPC .... A61H 2201/1635; A61H 2201/5007; A61H 2201/5043; A61H 2201/5064; A61H 2201/5069; A61H 2201/5079; A61B 5/11
See application file for complete search history.

(56) References Cited

U.S. PATENT DOCUMENTS

| | | | | |
|---|---|---|---|---|
| 2003/0093021 | A1* | 5/2003 | Goffer | A61F 5/0102 602/23 |
| 2007/0233403 | A1* | 10/2007 | Alwan | A61B 5/1038 702/33 |
| 2009/0298653 | A1* | 12/2009 | Rodetsky | A61H 3/04 482/69 |
| 2011/0184225 | A1* | 7/2011 | Whitall | A63B 24/0003 600/28 |
| 2013/0324890 | A1* | 12/2013 | Youssef | A61B 5/11 600/595 |
| 2014/0180173 | A1* | 6/2014 | Sullivan | A61B 5/0002 600/595 |
| 2016/0346156 | A1* | 12/2016 | Walsh | A63B 21/4009 |
| 2017/0311848 | A1* | 11/2017 | Wu | A61B 5/11 |

FOREIGN PATENT DOCUMENTS

| | | |
|---|---|---|
| EP | 2361734 A2 | 8/2011 |
| TW | I274239 B | 2/2007 |
| TW | 201335759 A1 | 9/2013 |

OTHER PUBLICATIONS

Nakagawa, et al., "Control of Intelligent Cane Robot Considering Usage of Ordinary Cane," in Proc. of 2013 IEEE RO-MAN: The 22nd IEEE International Symposium on Robot and Human Interactive Communication, Gyeongju, Korea, Aug. 26-29, 2013, pp. 762-767.

* cited by examiner

US 10,188,579 B2

METHOD FOR CONTROLLING A WALKING ASSISTANT APPARATUS

CROSS-REFERENCE TO RELATED APPLICATION

This application claims priority of Taiwanese Patent Application No. 105100238, filed on Jan. 6, 2016, the disclosure of which is incorporated herein in its entirety by reference.

FIELD

The disclosure relates to a method for controlling a walking assistant apparatus, and more particularly to a method for controlling a walking assistant apparatus by employing gathered information regarding gait of a user and force applied by the user.

BACKGROUND

A walking aid device may be designed to assist a user who cannot walk normally on his own or her own (e.g., one afflicted by Parkinson's disease).

Conventionally, a walking aid device may be categorized into one of a passive walking aid device and an active walking aid device. While a passive walking aid device, such as an assistive cane, is relatively lighter and easy to operate, the weight of the passive walking aid device must be carried by the user during a walk.

For example, when a user operates a quadricane in a walk, the user needs to move the quadricane to a position in front of the user to serve as a supporting point, before taking a step toward the supporting point. Additionally, after one or two steps, the user is required to move the quadricane again in order to continue walking.

An active walking aid device is typically equipped with a set of wheels, motors for driving the set of wheels, and means for detecting an intention of the user so as to move the active walking aid device accordingly.

A number of ways may be implemented for detecting the intention of the user. For example, one or more force detectors may be incorporated into the active walking aid device. Additionally, one or more laser detectors may be employed to detect gait of the user, in order to deduce the user's intention to move.

SUMMARY

An object of the disclosure is to provide a method for controlling a walking assistant apparatus.

According to one embodiment of the disclosure, the walking assistant apparatus includes a processor, a motion unit, a support unit that is disposed on the motion unit and that includes a handle component operable by a user, a first scanning device disposed on the support unit, and a torque sensor disposed on the handle component. The method includes the steps of:

a) scanning, by the first scanning device, the user so as to generate information associated with gait of the user;

b) detecting, by the torque sensor, a detected torque applied thereto about a vertical axis;

c) estimating, by the processor, a moving speed of the user based on the scanning information;

d) calculating, by the processor, a compliant motion speed based at least on the moving speed of the user, and a compliant rotational speed based on the detected torque detected in step b); and e) controlling, by the processor, the motion unit to move at the compliant motion speed and to turn at the compliant rotational speed so as to bring the walking assistant apparatus to move at the compliant motion speed and to turn at the compliant rotational speed.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
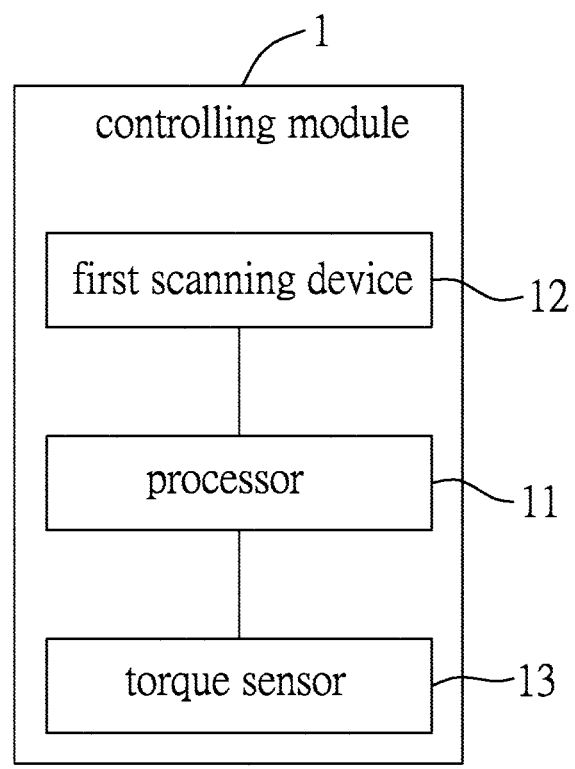
FIG. 1 is a block diagram illustrating a controlling module for controlling movement of a walking assistant apparatus, according to one embodiment of the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

FIG. 1 illustrates a controlling module 1 included in a walking assistant robot 2 (see FIG. 2) for controlling movement of the same, according to one embodiment of the disclosure. The controlling module 1 includes a processor 11, a first scanning device 12, and a torque sensor 13.

Figure 2:
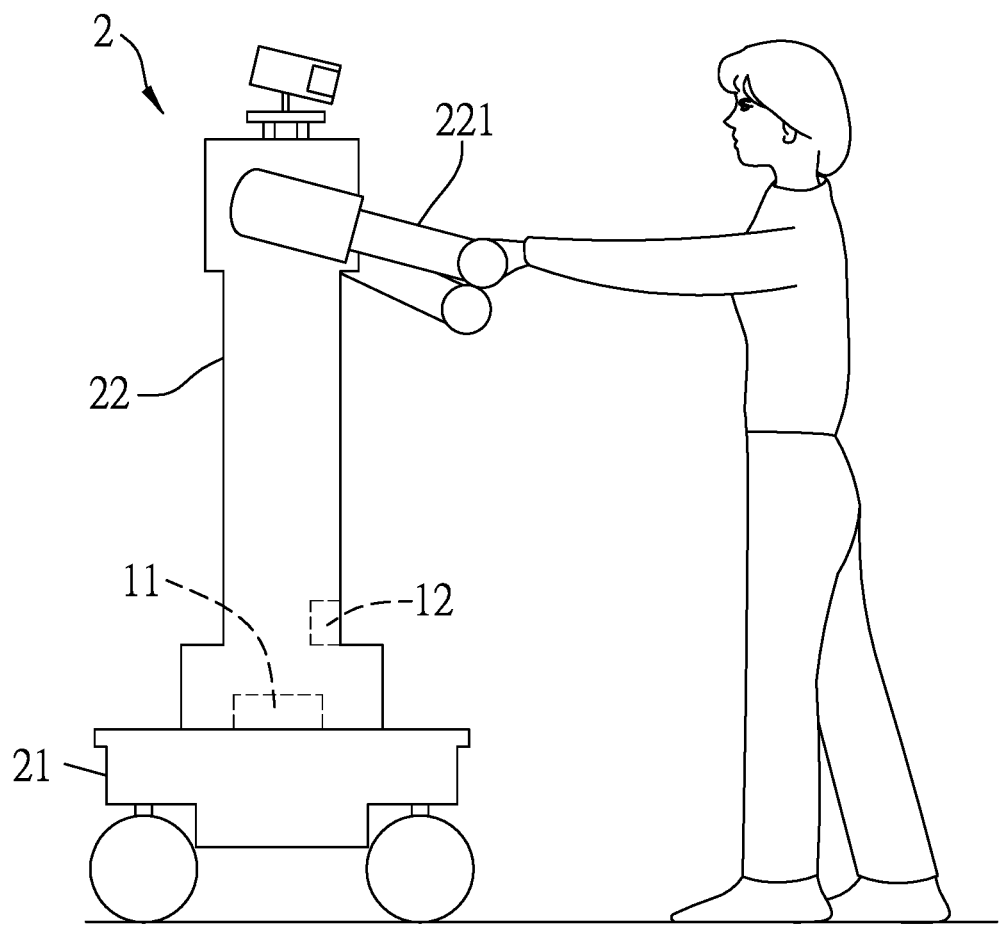
FIG. 2 illustrates a user operating the walking assistant apparatus.

As shown in FIG. 2, the walking assistant apparatus 2 includes a motion unit 21 and a support unit 22, and is implemented as a walking assistant robot.

The motion unit 21 includes a plurality of wheels and a plurality of motors for driving the wheels to move the walking assistant apparatus 2 in any direction.

The support unit 22 is disposed on the motion unit 21, and includes a handle component 221 operable by a user. In this embodiment, the support unit 22 is made to resemble an upper part of human body in form, including a torso part, two extending arm parts and a head part. The handle component 221 is disposed on one of the two arms for the user to handle.

The processor 11 may be embodied using a microcomputer or an industrial personal computer (IPC). The first scanning device 12 may be embodied using a laser scanner disposed on the torso part of the support unit 22, so as to perform scanning to detect a distance between the first scanning device 12 and an object, presumably a leg of the user.

Figure 3:
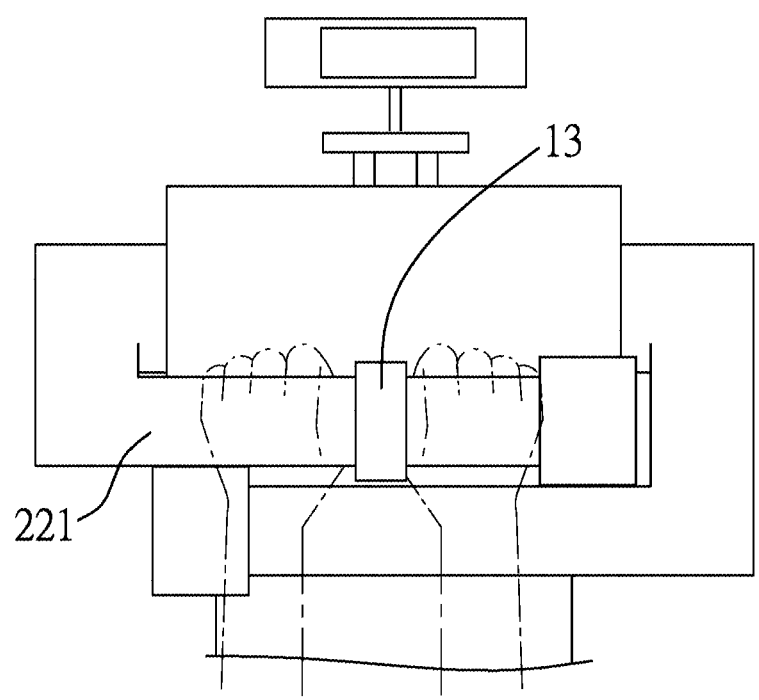
FIG. 3 illustrates the hands of the user handling the handle component of the walking assistant apparatus.
Figure 4:
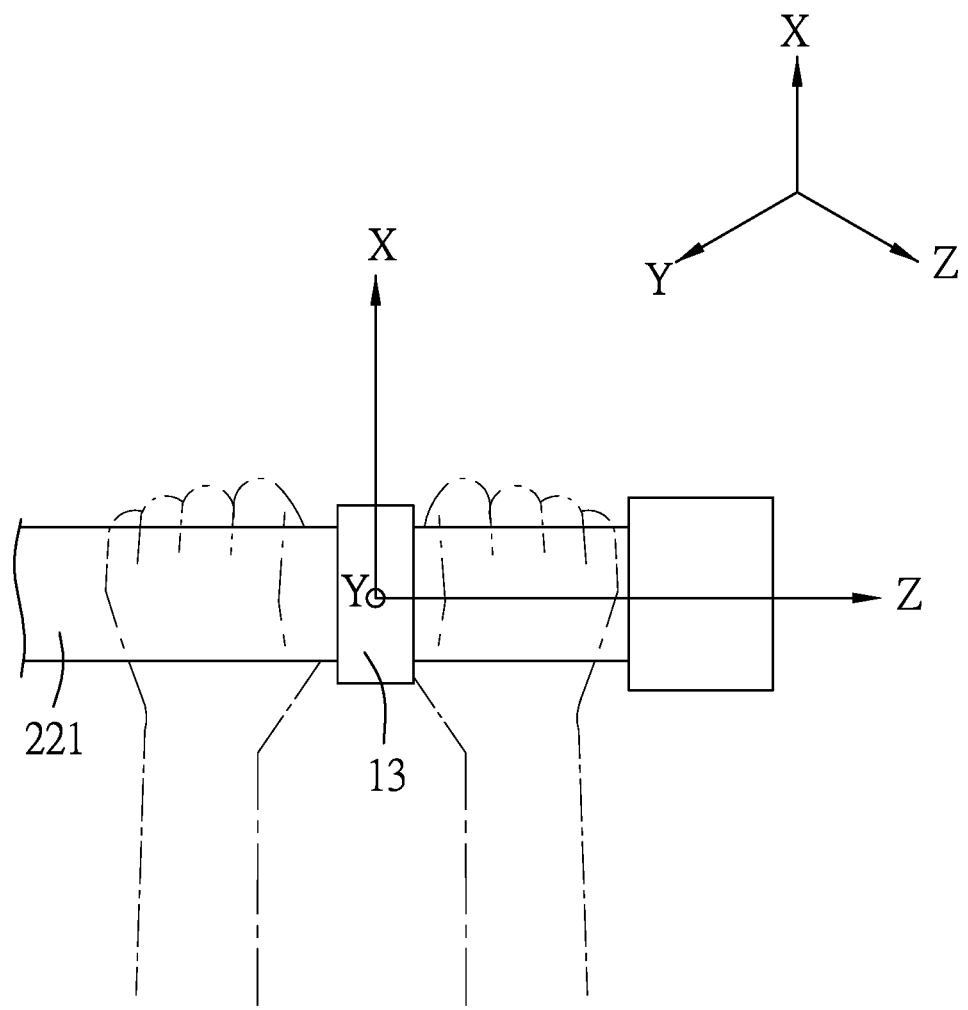
FIG. 4 illustrates a three-axis torque sensor and definition of the three axes.

The torque sensor 13 is disposed on the handle component 221. Referring to FIG. 3, the torque sensor 13 is disposed in a manner that when the user handles the handle component 221 using both hands, the torque sensor 13 is at a location between the hands of the user. Referring to FIG. 4, in this embodiment, the torque sensor 13 is embodied using a three-axis torque sensor, and the three axes are defined as follows: an X-axis is a vertical axis, a Y-axis is a front-rear axis with respect to the user when the user is looking at the torque sensor 13, and a Z-axis is an axial direction associated with the handle component 221.

Figure 5:
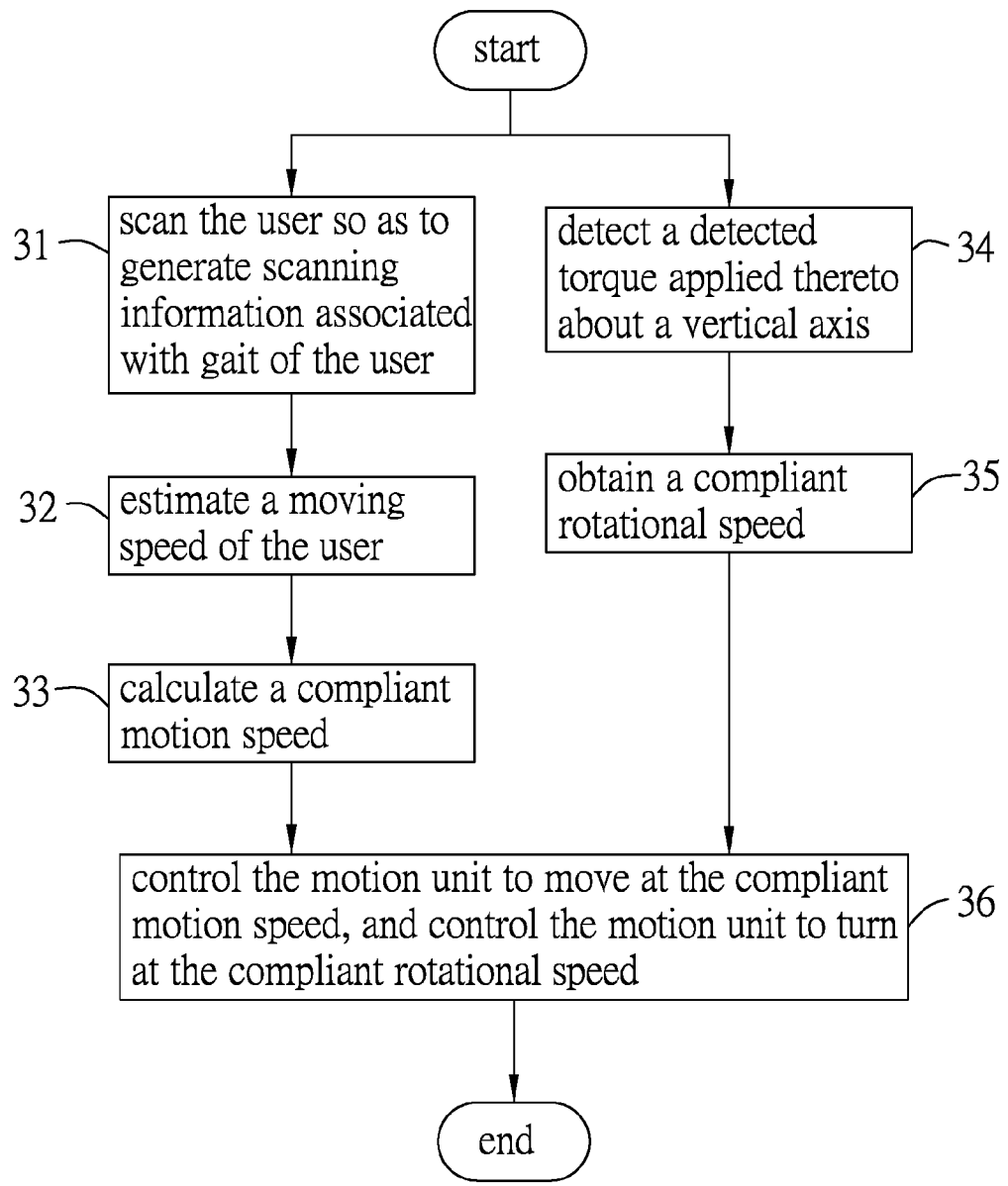
FIG. 5 is a flowchart illustrating steps of a method for controlling the walking assistant apparatus, according to one embodiment of the disclosure.

FIG. 5 is a flowchart illustrating steps of a method for controlling the walking assistant apparatus 2, according to one embodiment of the disclosure.

It is noted that, in order to control the walking assistant apparatus 2 to move correspondingly to an intention of the user (e.g., how fast the user intends to walk, what direction the user intends to turn to, etc.), the processor 11 needs to obtain associated information such as a compliant motion speed, a compliant rotation speed, etc.

As such, in step 31, the first scanning device 12 is controlled to scan the user so as to generate scanning information associated with gait of the user.

Specifically, the first scanning device 12 generates a first entry of distance information scanned at a first time instance (t−1), and a second entry of distance information scanned at a second time instance (t) after the first time instance (t−1).

Figure 6:
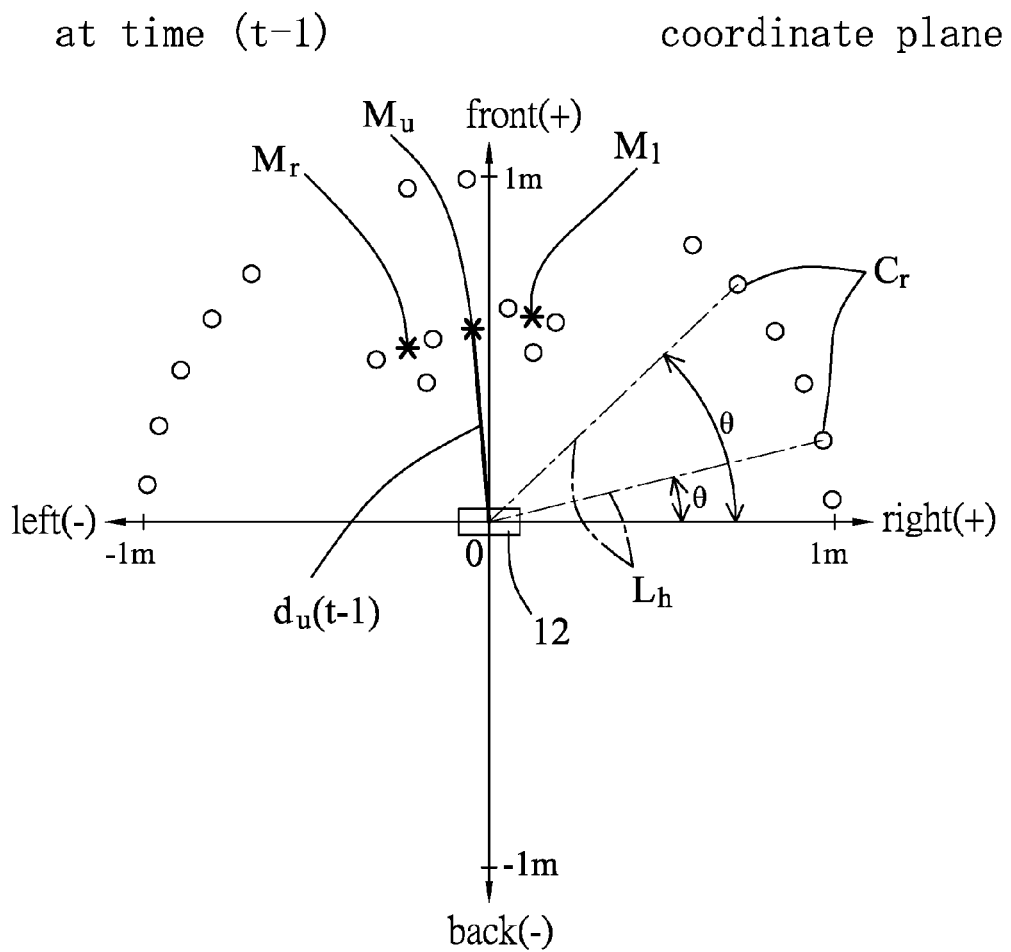
FIG. 6 illustrates calculation of a first distance between the user and a first scanning device at a first time instance, according to one embodiment of the disclosure.

As shown in FIG. 6, the first scanning device 12 is configured to perform a 180-degree scan of an area in front, and obtain a scanned distance every degree. This scan is performed at the first time instance (t−1) and the second time instance (t).

The first entry of distance information obtained by the scan may include a plurality of laser distances ($L_h$) and a plurality of scanned angles θ each corresponding to a respective one of the laser distances ($L_h$). In FIG. 6, the first entry of distance information defines a coordinate plane, with the first scanning device 12 serving as an origin of the coordinate plane. Each of the laser distances ($L_h$) and the corresponding one of the scanned angles θ may then yield a coordinate position ($C_r$).

In this embodiment, a laser ray emitted by the first scanning device 12 is able to travel one meter, which is defined as a maximum laser distance.

Figure 7:
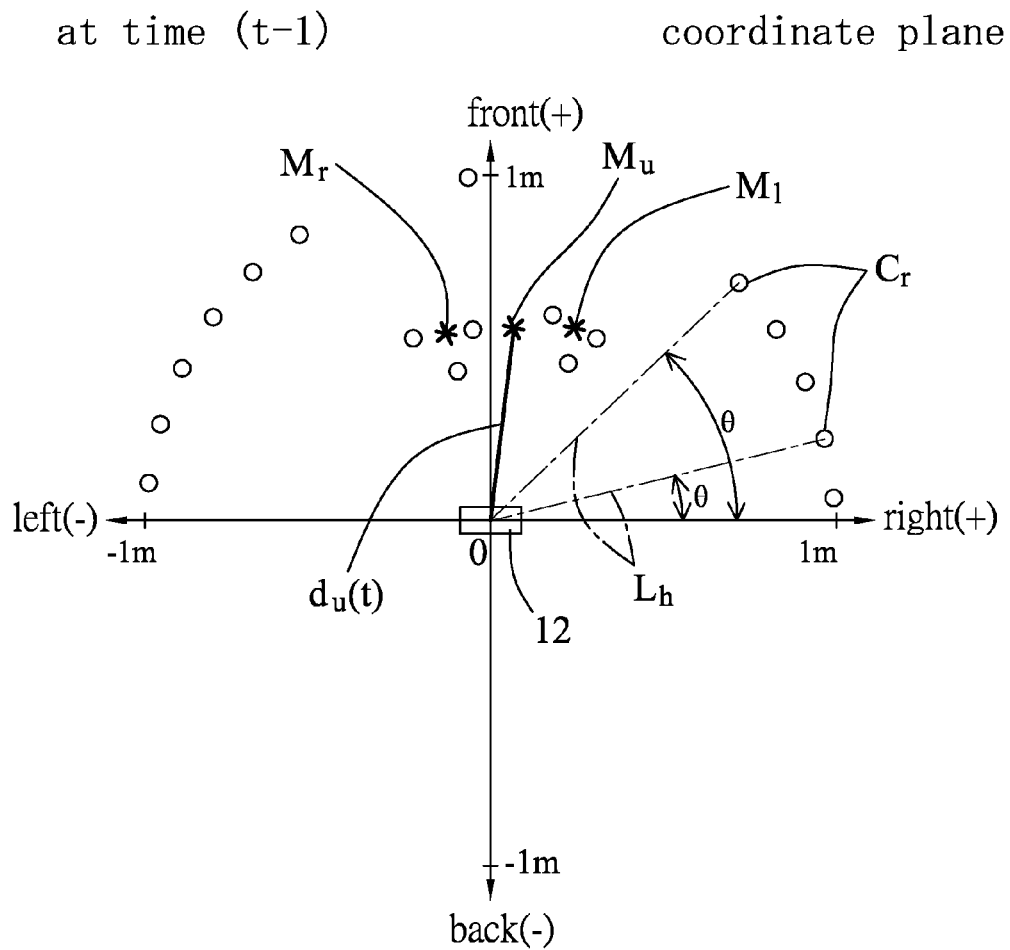
FIG. 7 illustrates calculation of a second distance between the user and the first scanning device at a second time instance, according to one embodiment of the disclosure.

FIG. 7 illustrates the first scanning device 12 performing the scan in the second time instance (t). The second entry of distance information defines a same coordinate plane.

In step 32, the processor 11 is programmed to calculate a first distance $d_u(t-1)$ (see FIG. 6) between the first scanning device 12 and the user at the first time instance (t−1) based on the first entry of distance information, to calculate a second distance $d_u(t)$ (see FIG. 7) between the first scanning device 12 and the user at the second time instance (t) based on the second entry of distance information, and to estimate a moving speed of the user.

Specifically, for calculating the first distance $d_u(t-1)$, the following process is employed. Referring back to FIG. 6, the processor 11 calculates a difference between one of the laser distances ($L_1$) and an immediately subsequent one of the laser distances ($L_2$), expressed by the term $|L_2-L_1|$. When this difference is larger than a predetermined threshold, the processor 11 determines that an edge of an object is detected. Since in this embodiment, the user has two legs, and each of the legs has two associated edges (one to appear, one to disappear during the scan), four such detections will be made.

As a result, two coordinate positions may be detected to serve as different edge points of a left leg of the user. Subsequently, a centre of a line segment defined by the two coordinate positions is calculated as a location of the left leg of the user on the coordinate plane, and assigned a first coordinate set ($M_l$).

A similar process is applied to detect two coordinate positions serving as two different edge points of a right leg of the user. Subsequently, a centre of a line segment defined by the two coordinate positions is calculated as a location of the right leg of the user on the coordinate plane, and assigned a second coordinate set ($M_r$).

Next, the location of the user at the first time instance (t−1) may be obtained by calculating a centre of a line segment defined by the first coordinate set ($M_l$) and the second coordinate set ($M_r$) to serve as the location of the user ($M_u$). The first distance $d_u(t-1)$ may then be obtained from the location of the user ($M_u$) with respect to the origin.

A similar process may be applied to the second entry of distance information, as illustrated by FIG. 7. As a result, a location of the user ($M_u$) at the second time instance (t) and the second distance $d_u(t)$ may be obtained. Using the first and second distances $d_u(t-1)$ and $d_u(t)$, a moving speed of the user may be estimated using the following equation:

$$\vec{V}_u(t) = \frac{d_u(t) - d_u(t-1)}{\Delta t}$$

where $\vec{V}_u(t)$ represents the moving speed of the user, and Δt represents a difference between the first time instance (t−1) and the second time instance (t) and is for instance 0.1 seconds.

In step 33, the processor 11 calculates a compliant motion speed based at least on the moving speed of the user.

Figure 8:
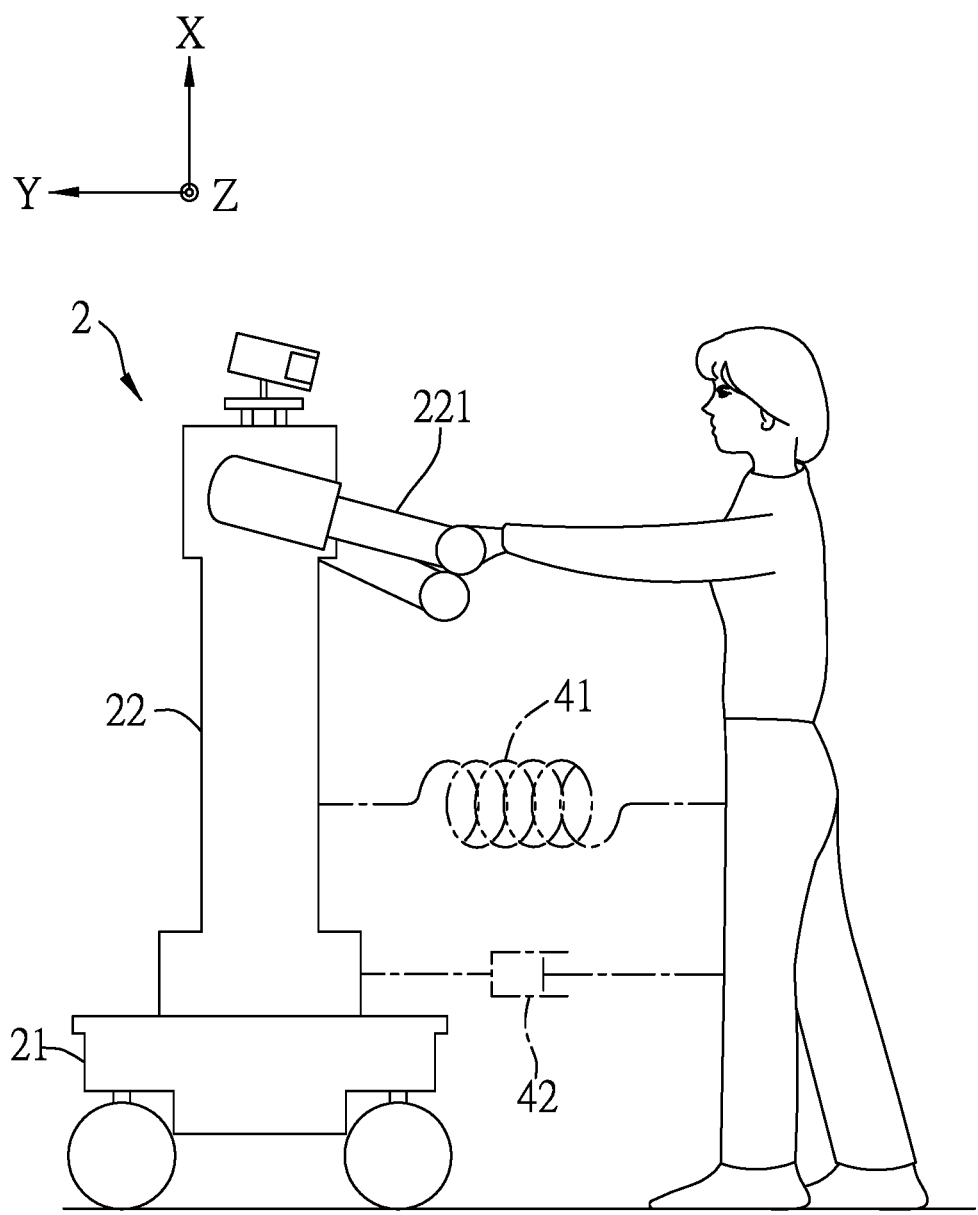
FIG. 8 illustrates a virtual mass-spring-damper system used for calculating a virtual force, according to one embodiment of the disclosure.

Specifically, as shown in FIG. 8, the processor 11 first calculates a virtual force for moving the walking assistant apparatus 2 based on the moving speed of the user and the second distance $d_u(t)$ in a mass-spring-damper system.

The mass-spring-damper system is employed for creating a scenario that the walking assistant apparatus 2 moves at a speed that is dictated by the moving speed of the user.

As such, a virtual spring 41 and a virtual damper 42 are provided to interconnect the walking assistant apparatus 2 and the user. When the walking assistant apparatus 2 is to be moved, it is assumed that the force needed (referred to as a virtual force) is provided by the virtual spring 41 and the virtual damper 42.

The virtual force is calculated by the following equation:

$$\vec{F}_{vir}(t) = \vec{B}_{vir} \vec{V}_u + k_{vir}(k_o - d_u)(t))$$

where $\vec{F}_{vir}(t)$ represents the virtual force, $B_{vir}$ represents a positive virtual damping coefficient of the virtual damper 41 in the mass-spring-damper system, $k_{vir}$ represents a positive virtual spring constant of the virtual spring 42 in the mass-spring-damper system, $\vec{V}_u(t)$ represents the moving speed of the user, $k_o$ represents an equilibrium length of the virtual spring 41 that corresponds with an arm length of the user, and $d_u(t)$ represents the second distance. That is to say, the virtual force is positively correlated to the moving speed of the user, and is negatively correlated to the second distance $d_u(t)$.

After the virtual force is obtained, the processor 11 is programmed to apply the virtual force to a first admittance model so as to obtain the compliant motion speed.

Specifically, the compliant motion speed is calculated using the following equation:

$$M_c \dot{\vec{V}}_r(t) + B_c \vec{V}_r(t) = \vec{F}_{vir}(t)$$

where $\vec{V}_r(t)$ represents the compliant motion speed, $M_c$ represents an expected mass in the mass-spring-damper system that is predetermined, and $B_c$ represents an expected damping coefficient of the virtual damper 42. It is noted that since the use of an admittance model to obtain the compliant motion speed is readily appreciated by ones skilled in the art, details regarding the admittance model are omitted herein for the sake of brevity.

While the above described steps 31 to 33 are implemented for obtaining the compliant motion speed, the processor 11 is further programmed to calculate a compliant rotational speed for controlling the walking assistant apparatus 2 to turn.

Specifically, in step 34, the torque sensor 13 detects, at the second time instance (t), a detected torque $\overline{M}_x(t)$ applied thereto about a vertical axis (the X-axis as defined above).

Figure 9:
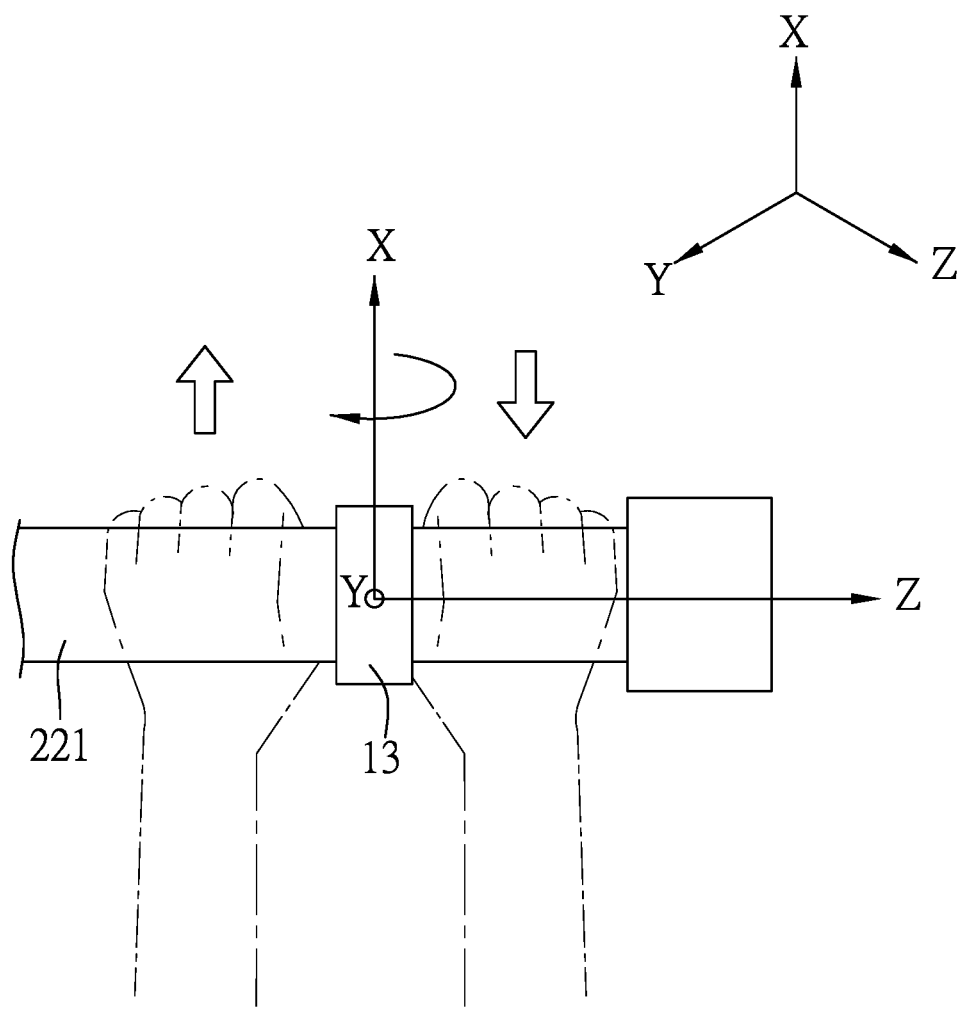
FIG. 9 illustrates the user, intending to turn right, and operating the handle component accordingly.
Figure 10:
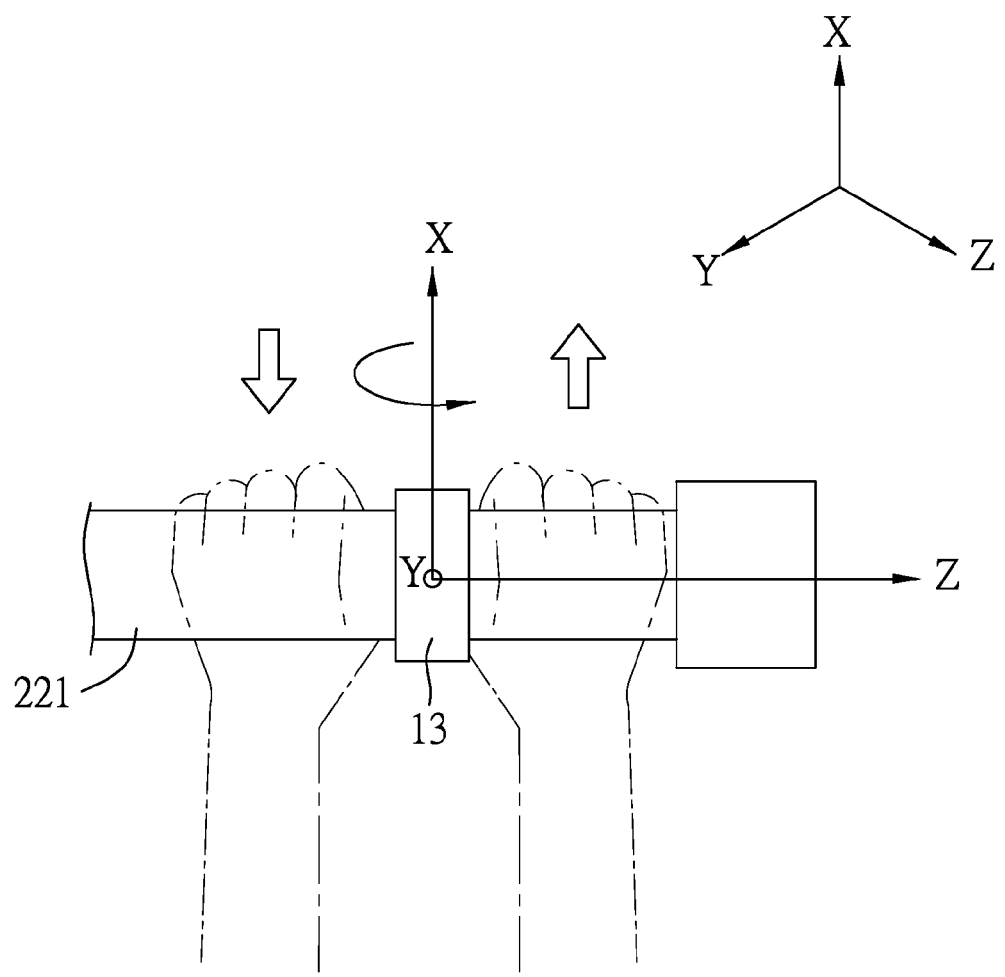
FIG. 10 illustrates the user, intending to turn left, and operating the handle component accordingly.

For example, in one instance as illustrated in FIG. 9, when the user operating the walking assistant apparatus 2 intends to turn right, the right hand of the user pulls a right-hand part of the handle component 221 backward (toward the user) and the left hand of the user pushes a left-hand part of the handle component 221 forward (away from the user). As a result, the detected torque detected by the torque sensor 13 is one that drives the handle component 221 to turn in a clockwise direction about the X-axis. Similarly, in another instance as illustrated in FIG. 10, when the user operating the walking assistant apparatus 2 intends to turn left, the right hand of the user pushes the right-hand part of the handle component 221 forward and the left hand of the user pulls the left-hand part of the handle component 221 backward. As a result, the detected torque detected by the torque sensor 13 is one that drives the handle component 221 to turn in a counterclockwise direction about the X-axis.

Then, in step 35, the processor 11 is programmed to apply the detected torque to a second admittance model so as to obtain the compliant rotational speed.

Specifically, the compliant rotational speed is calculated using the following equation:

$$I_a \dot{\vec{\omega}}_r(t) + B_a \vec{\omega}_r(t) = \vec{M}_x(t)$$

where $\vec{M}_x(t)$ represents the detected torque, $\vec{\omega}_r(t)$ represents the compliant rotational speed, $I_a$ represents an expected moment of inertia that is predetermined, and $B_a$ represents an expected damping coefficient of the virtual damper 42. It is noted that since the use of an admittance model to obtain the compliant rotational speed is readily appreciated by those skilled in the art, details regarding the admittance model are omitted herein for the sake of brevity.

After both the compliant motion speed and the compliant rotational speed are obtained, in step 36, the processor 11 controls the motion unit 21 to move at the compliant motion speed, and controls the motion unit 21 to turn at the compliant rotational speed. This in turn brings the walking assistant apparatus 2 to move at the compliant motion speed and to turn at the compliant rotational speed.

It is noted that the method as described above incorporates both the first scanning device 11 and the torque sensor 13 in an attempt to deduce the intention of the user operating the walking assistant apparatus 2. As a result, the walking assistant apparatus 2 implementing the method is capable of moving and turning in a speed that corresponds with the gait of the user.

For example, for a user afflicted with the Parkinson's disease (PD), his/her steps during a walk may abruptly become erratic due to the PD. In such a case, the walking assistant apparatus 2 may actively adjust the compliant motion speed and the compliant rotational speed in order to accommodate the change.

Figure 11:
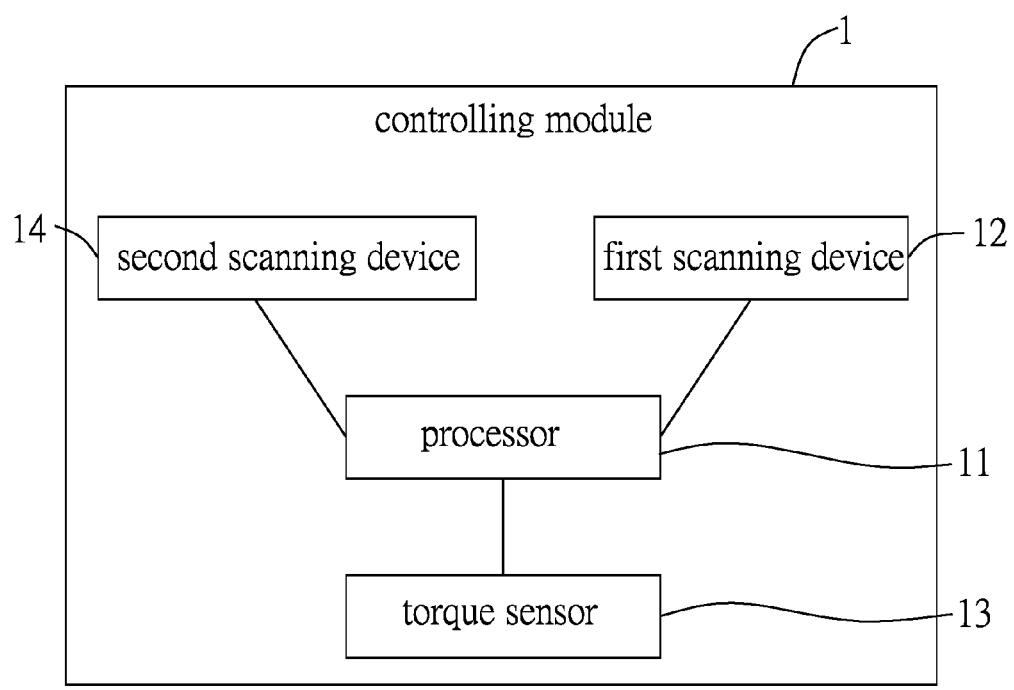
FIG. 11 is a block diagram illustrating a controlling module for controlling movement of a walking assistant apparatus, according to one embodiment of the disclosure.
Figure 12:
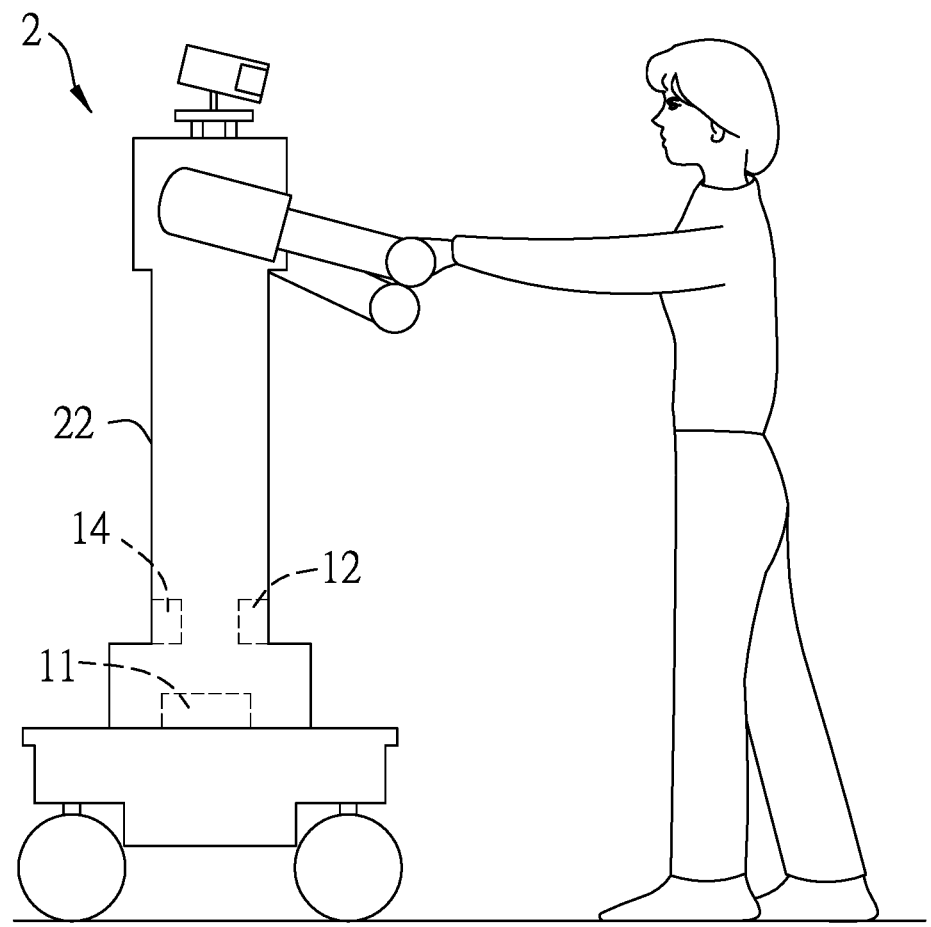
FIG. 12 illustrates a user operating the walking assistant apparatus, which incorporates a second scanning device.

FIG. 11 illustrates a controlling module 1 included in a walking assistant apparatus 2 (see FIG. 12) for controlling the movement of the same, according to one embodiment of the disclosure. The controlling module 1 includes a processor 11, a first scanning device 12, a torque sensor 13, and a second scanning device 14. In this embodiment, the second scanning device 14 is a laser scanner similar to the first scanning device 12, and is disposed on the support unit 22 opposite to the first scanning device 12 (that is, when the user operates the walking assistant apparatus 2, the first scanning device 12 faces the user, and the second scanning device 14 faces away from the user).

One object of the second scanning device 14 is to detect potential obstacles in front of the user while the user is walking. When the processor 11, aided by the detection of the second scanning device 14, determines that there exists an obstacle in front of the user, an auto avoidance procedure may be implemented in order to allow the walking assistant apparatus 2 to move automatically in an attempt to avoid the obstacle.

Figure 13:
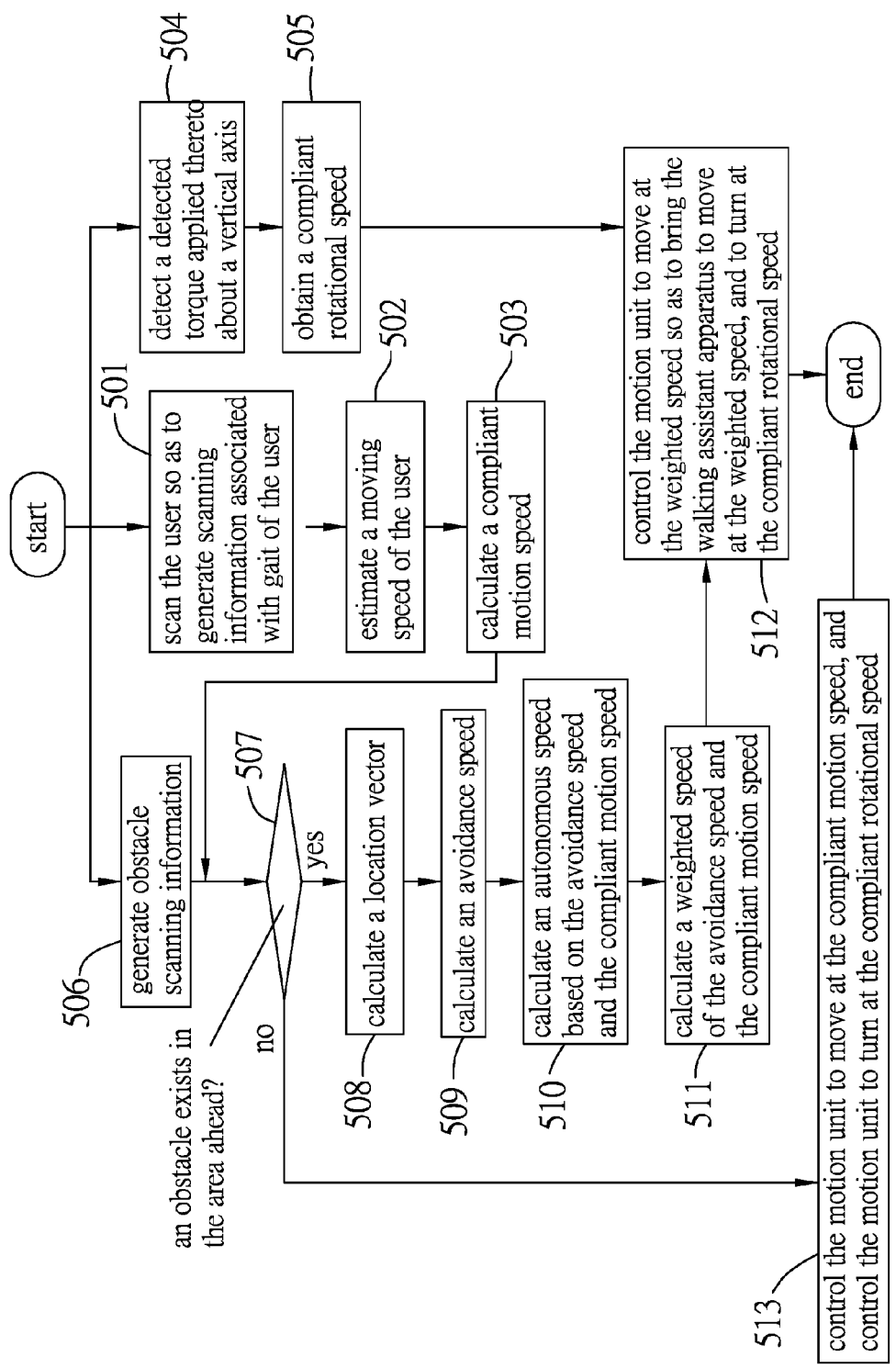
FIG. 13 is a flowchart illustrating steps of a method for controlling the walking assistant apparatus, according to one embodiment of the disclosure.

FIG. 13 is a flowchart illustrating steps of a method for controlling the walking assistant apparatus 2, according to one embodiment of the disclosure.

Specifically, steps 501 to 505 correspond respectively with steps 31 to 35 as illustrated in FIG. 5. In step 506, while the compliant motion speed and the compliant rotational speed are being calculated, the second scanning device 14 is configured to scan an area ahead of the walking assistant apparatus 2 in a moving direction thereof. In this manner, the second scanning device 14 is able to generate obstacle scanning information defining another coordinate plane, with the second scanning device 14 as an origin.

Figure 14:
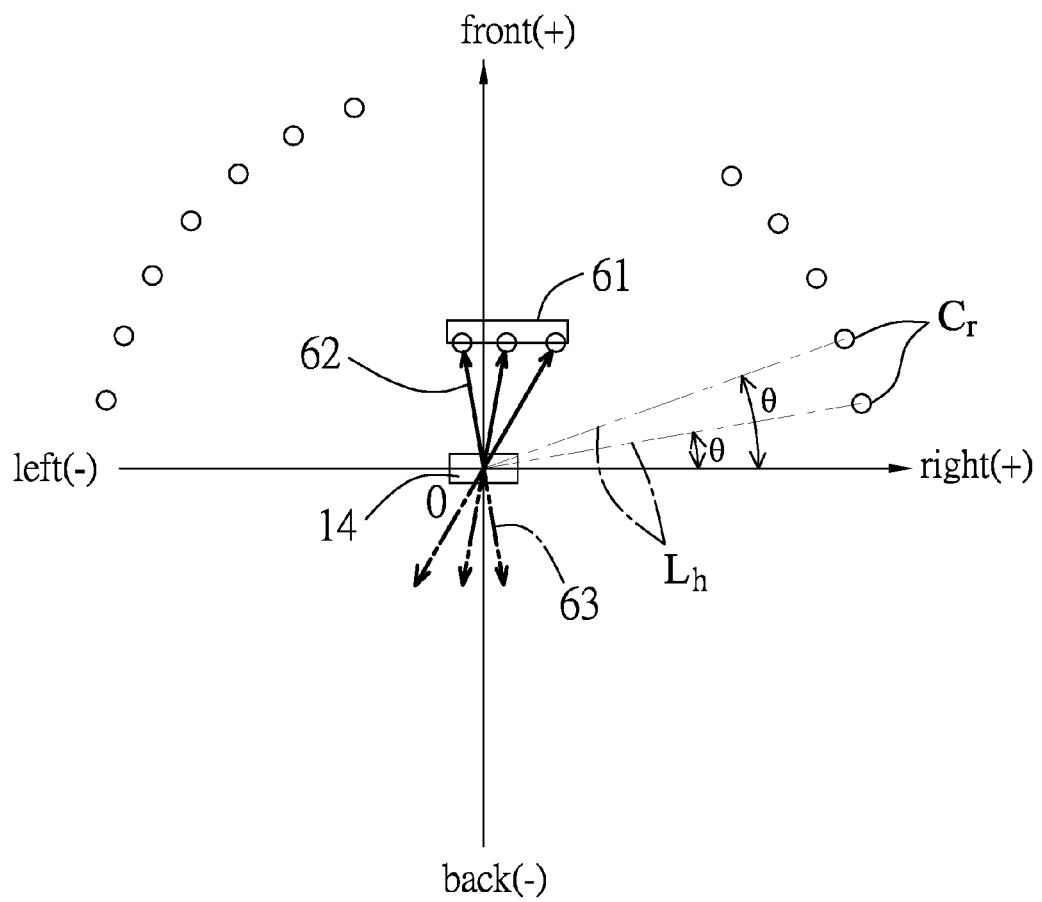
FIG. 14 illustrates the calculation of a location vector associated with an obstacle, according to one embodiment of the disclosure.

For example, FIG. 14 illustrates the second scanning device 14 performing the scan on the another coordinate plane thus defined. Similar to the manner in which the first scanning device 12 scans for detecting the legs of the user, the obstacle scanning information may include a plurality of laser distances ($L_h$) and a plurality of scanned angles ($\theta$) each corresponding to a respective one of the laser distances ($L_h$).

Each of the laser distances ($L_h$) and corresponding one of the scanned angles ($\theta$) may then yield a coordinate position ($C_r$).

Afterward, in step 507, the processor 11 determines whether an obstacle 61 exists in the area ahead. Specifically, for the example in FIG. 14, the processor 11 determines, for each of the laser distances ($L_h$), whether at least one of laser distances ($L_h$) is smaller than a predetermined distance. When that is the case, the processor determines that there exists at least one obstacle 61 is in the area ahead.

When it is determined by the processor 11 that at least one obstacle 61 is in the area ahead, the flow proceeds to step 508 in order to perform an avoidance process. Otherwise, the flow proceeds to step 513, which corresponds with step 36 of the method illustrated in FIG. 5 (that is to say, the walking assistant apparatus 2 is controlled to move at the compliant motion speed and to turn at the compliant rotational speed).

The avoidance process includes the following steps. In step 508, for each one of the laser distances ($L_h$) that is smaller than the predetermined distance, the processor 11 calculates a location vector 62 starting from a corresponding one of the coordinate positions ($C_r$) (i.e., the location of the at least one obstacle 61) and ending at a location of the second scanning device 14 in the another coordinate plane. The processor 11 further calculates an inverse location vector 63 that starts from the location of the second scanning device 14 in the another coordinate plane, projects in a direction opposite to the location vector 62, and has a magnitude that is identical with the location vector 62.

For example, as shown in FIG. 14, the processor calculates three location vectors 62, each associated with a respective one of the coordinate positions, and three corresponding inverse location vectors 63.

In step 509, the processor 11 calculates an avoidance speed $\vec{V}_o(t)$ that is positively correlated to the inverse location vectors 63.

Figure 15:
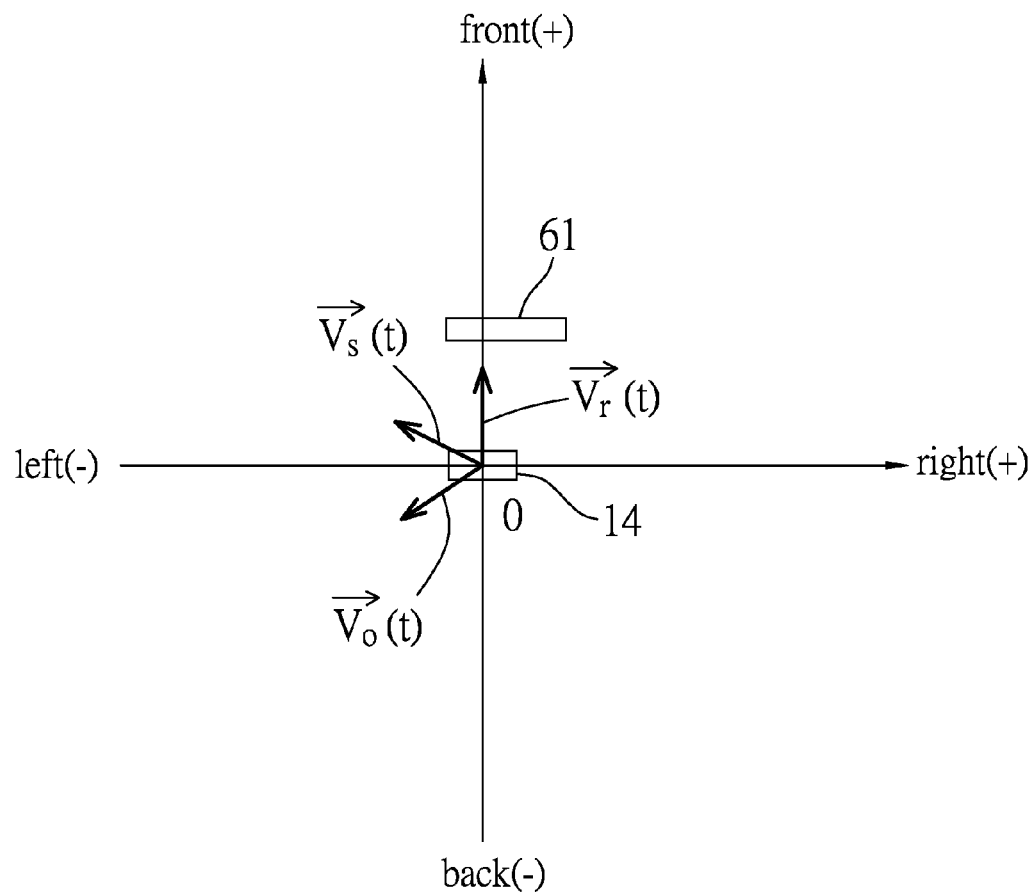
FIG. 15 illustrates the calculation of an autonomous speed based on an avoidance speed and a compliant motion speed, according to one embodiment of the disclosure.

Specifically, the avoidance speed $\vec{V}_o(t)$ is calculated using the following equation:

$$\vec{V}_o(t) = a \Sigma_i w_i(-\vec{x}_i(t))$$

where $\vec{x}_i(t)$ represents an $i^{th}$ one of the location vectors 62 (that is to say, $-\vec{x}_i(t)$ represents an $i^{th}$ one of the inverse location vectors 63), $w_i$ represents a weight associated with the $i^{th}$ one of the inverse location vectors 63, and is calculated using the equation $$w_i = \frac{D_{max} - |\vec{x}_i(t)|}{D_{max} \times |\vec{x}_i(t)|},$$

the parameter a represents a predetermined ratio, $D_{max}$ represents a predetermined maximum safety distance that is between the walking assistant apparatus 2 and the obstacle 61, and that is no larger than the maximum travelled distance. FIG. 15 illustrates a calculated avoidance speed $\vec{V}_o(t)$.

In step 510, the processor 11 calculates an autonomous speed $\vec{V}_s(t)$ based on the avoidance speed $\vec{V}_o(t)$ and the compliant motion speed $\vec{V}_r(t)$. Specifically, the autonomous speed $\vec{V}_s(t)$ is calculated using the equation $\vec{V}_s(t) = \vec{V}_o(t) + \vec{V}_r(t)$.

In step 511, the processor 11 calculates a weighted speed of the avoidance speed $\vec{V}_s(t)$ and the compliant motion speed $\vec{V}_r(t)$.

Specifically, the processor 11 assigns a weight to each of the autonomous speed $\vec{V}_s(t)$ and the compliant motion speed $\vec{V}_r(t)$, represented by the terms $G_r(t)$ (referred to as an autonomous weight) and $G_h(t)$ (referred to as a compliant weight), respectively. In this embodiment, $G_r(t) = 1 - G_h(t)$ (i.e., the sum of the weights assigned to the autonomous speed and the compliant motion speed equals 1).

Then, the weighted speed is calculated using the equation:

$$\vec{V}_w(t) = G_h(t) \times \vec{V}_r(t) + G_r(t) \times \vec{V}_s(t)$$

where $\vec{V}_w(t)$ represents the weighted speed.

In this embodiment, the compliant weight $G_h(t)$ is calculated using the equation $G_h(t) = Max(E_a(t), E_s(t))$, where $E_a(t)$ represents an avoidance confidence factor, and $E_s(t)$ represents a safety confidence factor.

The avoidance confidence factor $E_a(t)$ is calculated using the equation:

$$E_a(t) = \frac{|\vec{x}_a(t)|}{D_{max}}$$

where $\vec{x}_a(t)$ represents one of the location vectors 62 having a shortest length. That is to say, the compliant weight $G_h(t)$ may be positively correlated to one of the location vectors having a shortest length.

The avoidance confidence factor $E_a(t)$ serves as an indicator regarding how the user operating the walking assistant apparatus 2 is capable of avoiding the obstacle 61. Accordingly, as the distance between the walking assistant apparatus 2 and the obstacle 61 (represented by $\vec{x}_a(t)$) decreases, the avoidance confidence factor $E_a(t)$ decreases as well. On the other hand, as the distance between the walking assistant apparatus 2 and the obstacle 61 increases, the avoidance confidence factor $E_a(t)$ increases as well.

The safety confidence factor $E_s(t)$ is calculated using the equation:

$$E_s(t) = \left(1 - \frac{|\vec{V}_r(t)|}{|\vec{V}_{max}|}\right)^p$$

where (p) is a constant smaller than 1, and $\vec{V}_{max}$ represents a predetermined upper limit of the compliant motion speed $\vec{V}_r(t)$. That is to say, the compliant weight $G_h(t)$ may be negatively correlated to a value of the compliant motion speed $\vec{V}_r(t)$. The safety confidence factor $E_s(t)$ serves as an indicator regarding how the user operating the walking assistant apparatus 2 is capable of staying in a safe state. Accordingly, as the value of the compliant motion speed $|\vec{V}_r(t)|$ decreases, the safety confidence factor $E_s(t)$ increases. On the other hand, as the value of the compliant motion speed $|\vec{V}_r(t)|$ increases, the safety confidence factor $E_s(t)$ decreases.

It is noted that, the constant (p) is set to be smaller than 1 in order to ensure that the resulting safety confidence factor $E_s(t)$ is higher when the walking assistant apparatus 2 is moving at a slow speed.

In step 512, the processor 11 controls the motion unit 21 to move at the weighted speed so as to bring the walking assistant apparatus 2 to move at the weighted speed, and to turn at the compliant rotational speed.

From the above calculations, it may be apparent that when at least one of the avoidance confidence factor $E_a(t)$ and the safety confidence factor $E_s(t)$ is large enough, a determination that the user is capable of operating the walking assistant apparatus 2 properly may be made. As such, the compliant weight $G_h(t)$ is also high, reducing the interference applied to the walking assistant apparatus 2.

In brief, this embodiment detects whether an obstacle is present, and incorporates the avoidance process to determine whether the user is able to avoid the obstacle on his/her own. When it is determined that the user may not be able to avoid the obstacle (the distance is too short and/or the speed is too fast), the processor 11 intervenes to move the walking assistant apparatus 2 away from the obstacle.

To sum up, the method described in the disclosure utilizes the first scanning device 12 to obtain scanning information associated with gait of the user, and utilizes the torque sensor 13 to detect a detected torque applied thereto about the vertical axis. Using the above information, the processor 11 is able to deduce the intention of the user, and to accordingly calculate the compliant motion speed and the compliant rotational speed. Additionally, the avoidance process enables the processor 11 to bring the walking assistant apparatus 2 away from a detected obstacle under the assistance of the second scanning device 14, therefore rendering the operation of the walking assistant apparatus 2 safer.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding various inventive aspects.

In addition, this disclosure provides an autonomous obstacle avoidance mechanism; by combining the obstacle avoidance mechanism and the compliance controls, the walking-assistance apparatus is able to help user prevent from collisions with obstacles when walking in an environment with obstacles.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for controlling a walking assistant apparatus, the walking assistant apparatus including a processor, a motion unit, a support unit that is disposed on the motion unit and that includes a handle component operable by a user, a first scanning device disposed on the support unit, and a torque sensor disposed on the handle component, the method comprising the steps of:
   a) scanning, by the first scanning device, the user so as to generate scanning information associated with gait of the user;
   b) detecting, by the torque sensor, a detected torque applied thereto about a vertical axis;
   c) estimating, by the processor, a moving speed of the user based on the scanning information;
   d) calculating, by the processor, a compliant motion speed based at least on the moving speed of the user, and a compliant rotational speed based on the detected torque detected in step b); and
   e) controlling, by the processor, the motion unit to move at the compliant motion speed and to turn at the compliant rotational speed so as to bring the walking assistant apparatus to move at the compliant motion speed and to turn at the compliant rotational speed;
   wherein step a) includes scanning the user so as to generate the scanning information that includes a first entry of distance information scanned at a first time instance and a second entry of distance information scanned at a second time instance after the first time instance;
   wherein step c) includes the sub-steps of
      calculating a first distance between the first scanning device and the user at the first time instance based on the first entry of distance information,
      calculating a second distance between the first scanning device and the user at the second time instance based on the second entry of distance information, and
      calculating the moving speed of the user based on the first distance, the second distance and a difference between the first time instance and the second time instance; and
   step d) includes calculating the compliant motion speed based on the detected torque and the second distance.

2. The method of claim 1, wherein in step d), the compliant motion speed is positively correlated to the moving speed of the user, and is negatively correlated to the second distance.

3. The method of claim 1, the first scanning device being implemented using a laser scanner, wherein each of the sub-step of calculating a first distance and the sub-step of calculating a second distance includes, for a respective one of the first entry of distance information and the second entry of distance information defining a same coordinate plane,
   assigning a first coordinate set of a location of a left leg of the user on the coordinate plane, using the first scanning device as an origin of the coordinate plane;
   assigning a second coordinate set of a location of a right leg of the user on the coordinate plane;
   calculating a centre of a line segment defined by the first coordinate set and the second coordinate set to serve as a location of the user; and
   calculating a respective one of the first distance and the second distance based on the location of the user and the origin.

4. The method of claim 3, wherein step d) includes the sub-steps of:
   calculating a virtual force for moving the walking assistant apparatus based on the moving speed of the user and the second distance in a mass-spring-damper system,
   applying the virtual force to a first admittance model so as to obtain the compliant motion speed; and applying the detected torque to a second admittance model so as to obtain the compliant rotational speed.

5. The method of claim 4, wherein, in step d), the virtual force is calculated by the following equation:

$$\vec{F}_{vir}(t) = \vec{B}_{vir}\vec{V}_u + k_{vir}(k_o - d_u)(t))$$

where $\vec{F}_{vir}(t)$ represents the virtual force, $B_{vir}$ represents a virtual damping coefficient of a virtual damper in the mass-spring-damper system, $k_{vir}$ represents a virtual spring constant of a virtual spring in the mass-spring-damper system, $\vec{V}_u(t)$ represents the moving speed of the user, $k_o$ represents an equilibrium length of the virtual spring that corresponds with an arm length of the user, and $d_u(t)$ represents the second distance.

6. The method of claim 4, the walking assistant apparatus further including a second scanning device disposed on the support unit, the method further comprising the steps of:
   f) scanning, by the second scanning device, an area ahead of the walking assistant apparatus in a moving direction thereof so as to generate obstacle scanning information defining another coordinate plane;
   g) determining, by the processor, whether an obstacle is in the area, according to the obstacle scanning information;
   h) when it is determined by the processor that at least one obstacle is in the area, performing, by the processor, an avoidance process that includes the steps of
      i) calculating, by the processor, a location vector starting from a location of the second scanning device and ending at a location of the at least one obstacle in the coordinate plane, and an avoidance speed that is positively correlated to the location vector,
      ii) calculating, by the processor, an autonomous speed based on the avoidance speed and the compliant motion speed,
      iii) calculating, by the processor, a weighted speed of the avoidance speed and the compliant motion speed by assigning a weight to each of the autonomous speed and the compliant motion speed, and
      iv) controlling, by the processor, the motion unit to move at the weighted speed so as to bring the walking assistant apparatus to move at the weighted speed.

7. The method of claim 6, wherein step i) includes:
calculating, by the processor, a plurality of location vectors each from a location of a portion of the at least one obstacle and ending at the location of the second scanning device in the coordinate plane, and further assigning a weight to each of the location vectors, the weight being negatively correlated to a length of the location vector; and
the avoidance speed is positively correlated to a weighted sum of the location vectors.

8. The method of claim 7, wherein in step iii), the weight assigned to the autonomous speed is positively correlated to one of the location vectors having a shortest length, and a sum of the weights assigned to the autonomous speed and the compliant motion speed equals 1.

9. The method of claim 7, wherein in step iii), the weight assigned to the compliant motion speed is negatively correlated to a value of the compliant motion speed, and a sum of the weights assigned to the autonomous speed and the compliant motion speed equals 1.

10. The method of claim 6, wherein step ii) includes adding the avoidance speed and the compliant motion speed to obtain the autonomous speed.

* * * * *